United States Patent
Abou Mahmoud et al.

(10) Patent No.: US 10,886,027 B2
(45) Date of Patent: Jan. 5, 2021

(54) PREDICTING ENGAGEMENT ITEMS FOR CARE PROVIDERS

(71) Applicant: International Business Machines Corporation, Armonk, NY (US)

(72) Inventors: Alaa Abou Mahmoud, Dracut, MA (US); Paul R. Bastide, Boxford, MA (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 555 days.

(21) Appl. No.: 15/709,796

(22) Filed: Sep. 20, 2017

(65) Prior Publication Data
US 2019/0087543 A1 Mar. 21, 2019

(51) Int. Cl.
*G06Q 50/22* (2018.01)
*G06Q 10/10* (2012.01)
(Continued)

(52) U.S. Cl.
CPC .......... *G16H 50/20* (2018.01); *G06F 16/951* (2019.01); *G06F 40/30* (2020.01); *G16H 40/20* (2018.01);
(Continued)

(58) Field of Classification Search
CPC .......... G06Q 10/0631; G06Q 10/1095; G06Q 50/24; G06Q 10/06; G06Q 20/14;
(Continued)

(56) References Cited

U.S. PATENT DOCUMENTS

| 7,711,582 B2 | 5/2010 | Duckert et al. |
| 8,275,803 B2 | 9/2012 | Brown et al. |

(Continued)

OTHER PUBLICATIONS

"Lay Health Beliefs and Illness Behaviour", Public Health Action Support Team (PHAST) 2017, Health Knowledge, http://www.healthknowledge.org.uk/public-health-textbook/medical-sociology-policyeconomics/4a-concepts-health-illness/section4, Public Health Textbook, Concepts of Health and Illness: Section 4, retrieved from the intenet Feb. 23, 2016, 7 pages.

(Continued)

*Primary Examiner* — Maroun P Kanaan
(74) *Attorney, Agent, or Firm* — Stephen R. Tkacs; Stephen J. Walder, Jr.; William J. Stock

(57) ABSTRACT

A mechanism is provided in a data processing system to implement a healthcare cognitive system which operates for predicting engagement items for care providers. An engagement item prediction component executing within the healthcare cognitive system detects a scheduled appointment between a patient and a doctor. The engagement item prediction component scans communication pattern and details of patient communications for indicators of a medical condition of the patient. The healthcare cognitive system generates a set of one or more questions related to the medical condition. The engagement item prediction component presents the set of one or more questions to the user and receives one or more responses to the set of one or more questions from the patient. The healthcare cognitive system generates one or more seed topics based on the one or more responses and presents the one or more seed topics to the doctor for the scheduled appointment.

20 Claims, 4 Drawing Sheets

(51) Int. Cl.
G16H 50/20 (2018.01)
G06F 16/951 (2019.01)
G16H 40/20 (2018.01)
G06F 40/30 (2020.01)
G06F 19/00 (2018.01)
G06Q 50/00 (2012.01)
G16H 10/20 (2018.01)
G16H 10/60 (2018.01)

(52) U.S. Cl.
CPC ......... *G06F 19/324* (2013.01); *G06Q 10/107* (2013.01); *G06Q 10/1095* (2013.01); *G06Q 50/01* (2013.01); *G16H 10/20* (2018.01); *G16H 10/60* (2018.01)

(58) Field of Classification Search
CPC ........ G16H 10/20; G16H 10/60; G16H 50/20; G16H 40/20; G16H 40/63; G16H 15/00; G16H 20/40; G16H 40/67; G16H 50/50; G16H 50/70; G16H 80/00; G06F 16/24; G06F 16/3344; G06F 3/0481; G06F 19/00
See application file for complete search history.

(56) References Cited

U.S. PATENT DOCUMENTS

| | | | |
|---|---|---|---|
| 8,758,238 | B2 | 6/2014 | Clapp |
| 2009/0287678 | A1 | 11/2009 | Brown et al. |
| 2010/0161348 | A1 | 6/2010 | Lindell et al. |
| 2011/0066587 | A1 | 3/2011 | Ferrucci et al. |
| 2011/0125734 | A1 | 5/2011 | Duboue et al. |
| 2013/0007055 | A1 | 1/2013 | Brown et al. |
| 2013/0018652 | A1 | 1/2013 | Ferrucci et al. |
| 2013/0066886 | A1 | 3/2013 | Bagchi et al. |
| 2014/0122109 | A1 | 5/2014 | Ghanbari et al. |
| 2014/0278528 | A1 | 9/2014 | Simha et al. |
| 2017/0262604 | A1* | 9/2017 | Francois ............. G06F 19/3418 |

OTHER PUBLICATIONS

Braunack-Mayer, Annette et al., "Before the consultation: why people do (or do not) go to the doctor", Royal College of General Practitioners, http://www.ncbi.nlm.nih.gov/pmc/articles/PMC2702011, British Journal of General Practice, vol. 59, No. 564, Jul. 1, 2009, 3 pages.

Evans, Julie et al., ""It can't be very important because it comes and goes"—patients' accounts of intermittent symptoms preceding a pancreatic cancer diagnosis: a qualitative study", BMJ Publishing Group Limited, http://www.ncbi.nlm.nih.gov/pmc/articles/PMC3932002/, BMJ Open, vol. 4, No. 2, Feb. 1, 2014, 13 pages.

Green, Carla A. et al., "Seeking, Delaying and Avoiding Routine Health Care Services: Patient Perspectives", HHS Public Access, http://www.ncbi.nlm.nih.gov/pmc/articles/PMC3933475/, American Journal of Health Promotion, vol. 28, No. 5, May-Jun. 2014, 12 pages.

High, Rob, "The Era of Cognitive Systems: An Inside Look at IBM Watson and How it Works", IBM Corporation, Redbooks, Dec. 12, 2012, 16 pages.

Lacy, Naomi L. et al., "Why We Don't Come: Patient Perceptions on No-Shows", American Academy of Family Physicians, http://www.ncbi.nlm.nih.gov/pmc/articles/PMC1466756/, Annals of Family Medicine, vol. 2, No. 6, Jan. 23, 2004, 7 pages.

McCord, M.C. et al., "Deep parsing in Watson", IBM J. Res. & Dev, vol. 56 No. 3/4 Paper 3, May/Jul. 2012, pp. 3:1-3:15.

Mehrotra, Ateev et al., "Implementing open-access scheduling of visits in primary care practices: a cautionary tale", National Center for Biotechnology Information, http://www.ncbi.nlm.nih.gov/pubmed/18559842, Ann Intern Med, vol. 148, No. 2, Abstract only, Jun. 17, 2008, 2 pages.

O'Hare, MD, C. D. et al., "The Outcomes of Open-Access Scheduling", American Academy of Family Physicians, http://www.aafp.org/fpm/2004/0200/p35.pdf, Family Practice Management Web, vol. 11, No. 2, Feb. 2004, 4 pages.

Rabin, Roni C., "You're on the clock: Doctors rush patients out the door", Kaiser Health News, https://www.usatoday.com/story/news/nation/2014/04/20/doctor-visits-time-crunch-health-care/7822161/, Apr. 20, 2014, 2 pages.

Smith, James A. et al., "What do we know about men's helpseeking and health service use?", Medical Journal of Australia, https://www.mja.com.au/journal/2006/184/2/what-do-we-know-about-men-s-help-seeking-and-health-service-use, Viewpoint, vol. 184, No. 2, Jan. 16, 2006, 6 pages.

Tai-Seale, Ming et al., "Time Allocation in Primary Care Office Visits", Health Research and Educational Trust, http://www.ncbi.nlm.nih.gov/pmc/articles/PMC2254573, Health Services Research, vol. 42, No. 5, Oct. 2007, 14 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

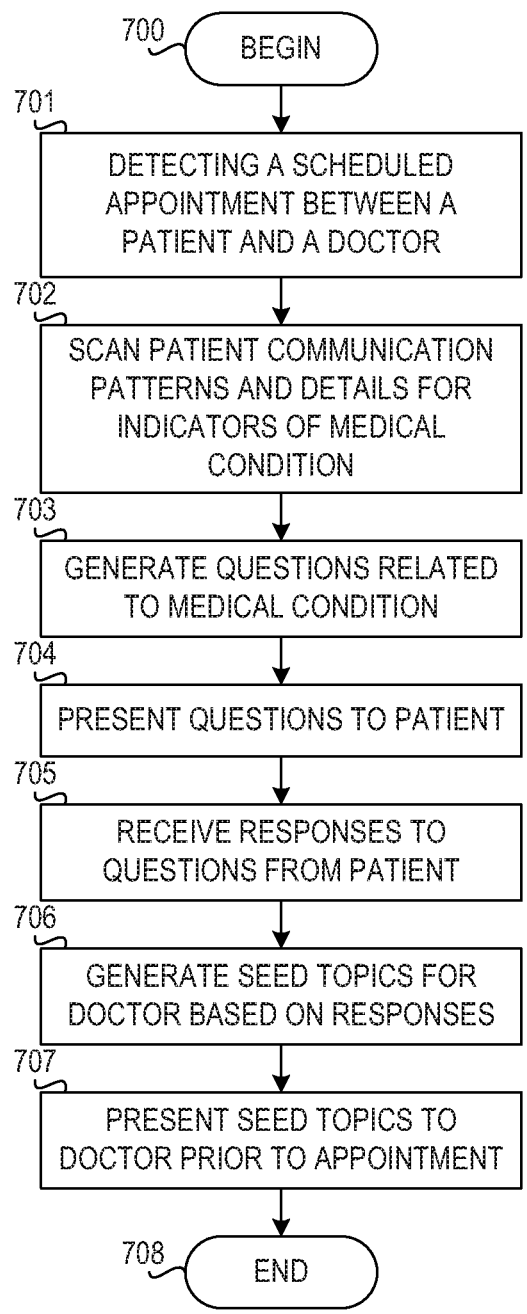

PREDICTING ENGAGEMENT ITEMS FOR CARE PROVIDERS

BACKGROUND

The present application relates generally to an improved data processing apparatus and method and more specifically to mechanisms for predicting engagement items for care providers.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions which are executed by the at least one processor and configure the processor to implement a healthcare cognitive system which operates for predicting engagement items for care providers. The method comprises detecting, by an engagement item prediction component executing within the healthcare cognitive system, a scheduled appointment between a patient and a doctor. The method further comprises scanning, by the engagement item prediction component, communication pattern and details of patient communications for indicators of a medical condition of the patient. The method further comprises generating, by the healthcare cognitive system, a set of one or more questions related to the medical condition. The method further comprises presenting, by engagement item prediction component, the set of one or more questions to the user and receiving, by the engagement item prediction component, one or more responses to the set of one or more questions from the patient. The method further comprises generating, by the healthcare cognitive system, one or more seed topics based on the one or more responses and presenting, by the healthcare cognitive system, the one or more seed topics to the doctor for the scheduled appointment.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 7 is a flowchart illustrating operation of a mechanism for predicting engagement items for care providers in accordance with an illustrative embodiment.

DETAILED DESCRIPTION

Figure 1:
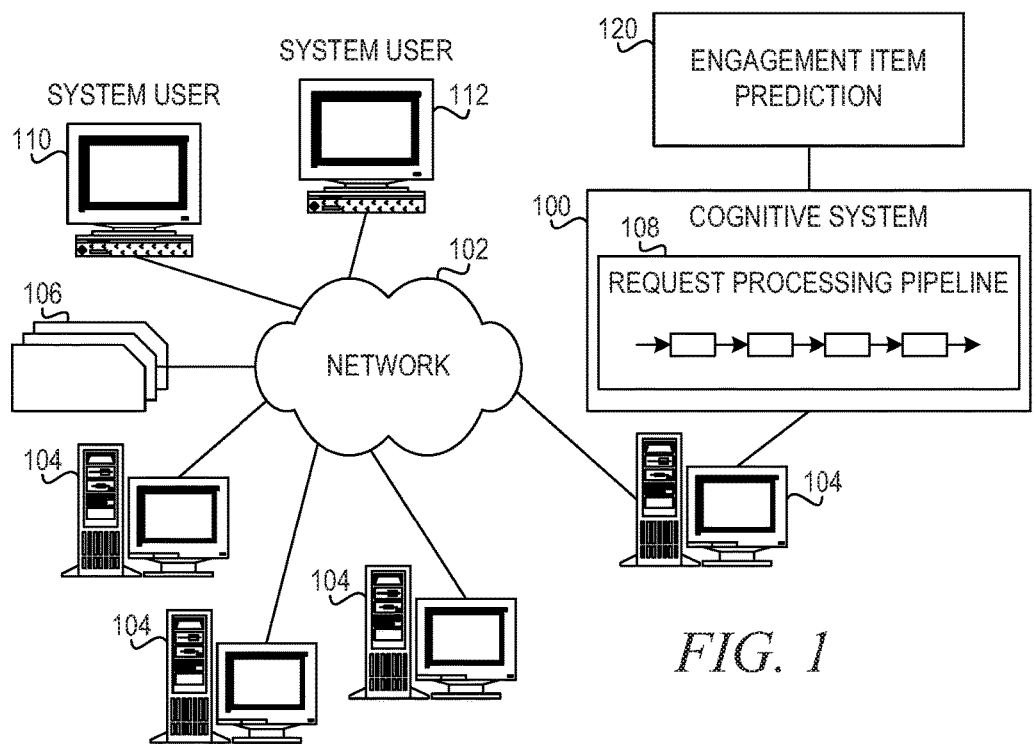
FIG. 1 depicts a schematic diagram of one illustrative embodiment of a cognitive system in a computer network.

Health problems are a major drain on the economy, resulting in millions of workers reporting missed days due to illness each year and reducing economic output by hundreds of billions of dollars per year. Increasing the use of proven preventive services can encourage greater workplace productivity.

Many doctors are limited with the amount of time they are able to devote to a single patient. The median time spent with a patient by a doctor is under sixteen minutes. The illustrative embodiments provide a mechanism to prepare and optimize care providers' engagement items during the limited time spent with the patient.

The illustrative embodiments provide mechanism for predicting and confirming items for a patient/doctor encounter. The mechanism detects a pending scheduled medical appointment for a patient, scans the patient's communication patterns and details, prompts the patient with a series of questions based on the communication patterns and details, analyzes the responses to the questions, and presents seed topics to the doctor for the appointment. The mechanism of the illustrative embodiments may provide a trajectory of prompts and responses. In one embodiment, the mechanism may use a pain scale or body reference to indicate pain points. In another embodiment, the mechanism may prompt the user on a repeated schedule. The mechanism may be employed at primary care, walk-in clinics, emergency services, or specialists.

The illustrative embodiments shorten the time to reconcile issues in a conversation. The illustrative embodiments ensure that important items or issues are covered during the doctor-patient interaction. The illustrative embodiments aid doctors when a user has no patient history or even a limited knowledge of the native language.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
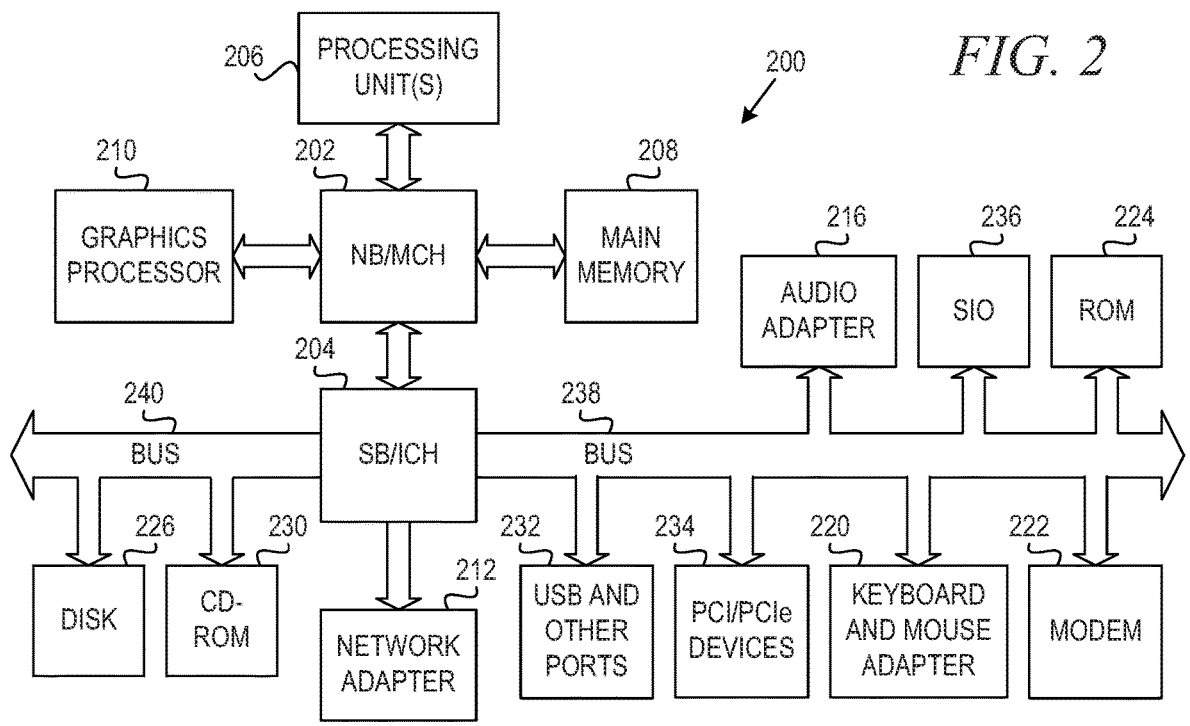
FIG. 2 is a block diagram of an example data processing system in which aspects of the illustrative embodiments are implemented.
Figure 3:
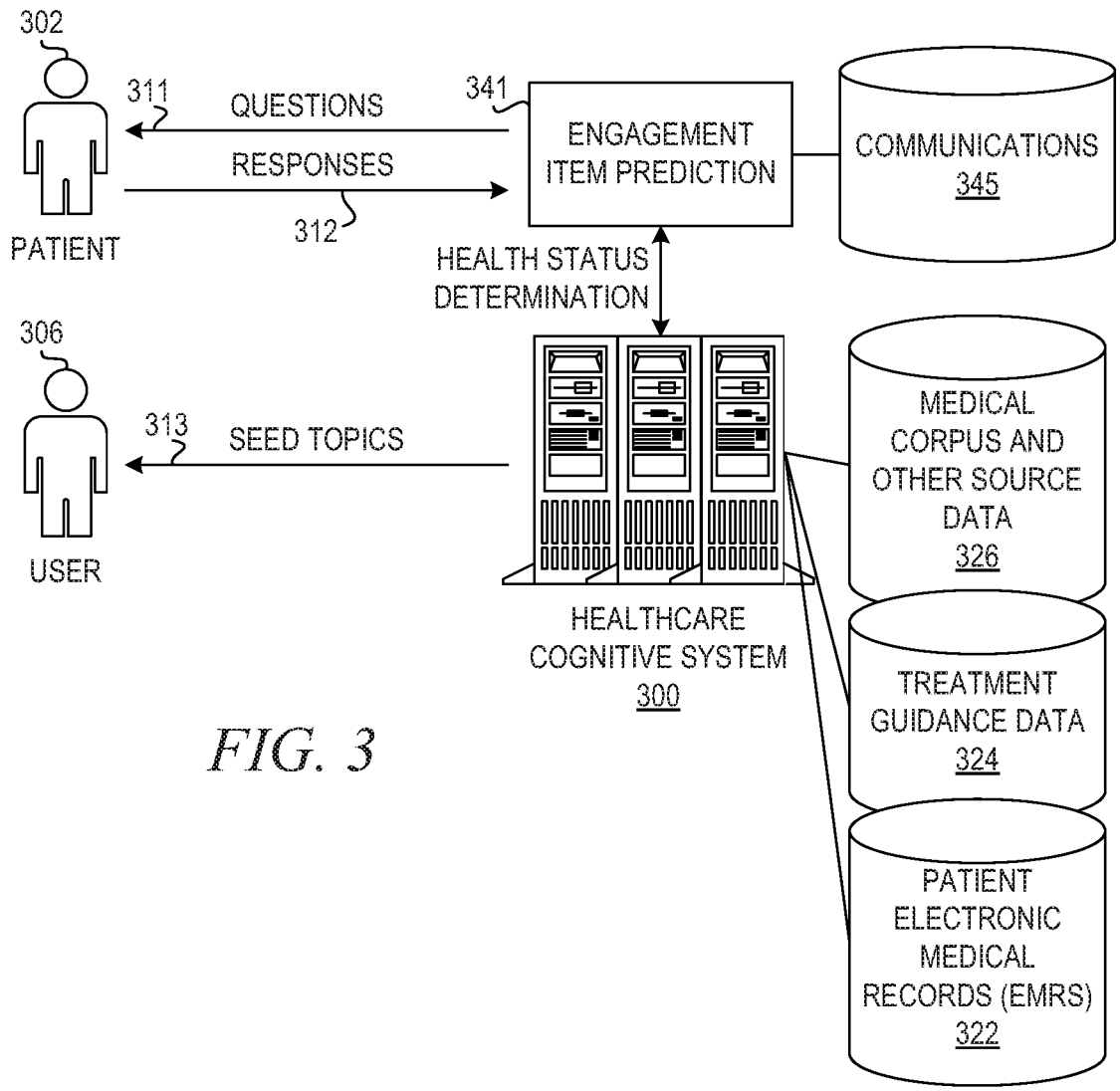
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing medical treatment recommendations for patients based on their specific features as obtained from various sources, e.g., patient electronic medical records (EMRs), patient questionnaires, etc. In particular, the mechanisms of the present invention provide a mechanism for verification of clinical hypothetical statements based on dynamic cluster analysis.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support, different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have its own associated corpus or corpora that it ingests and operates on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson® is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding
   Ingest and process vast amounts of structured and unstructured data
   Generate and evaluate hypotheses
   Weigh and evaluate responses that are based only on relevant evidence
   Provide situation-specific advice, insights, and guidance
   Improve knowledge and learn with each iteration and interaction through machine learning processes
   Enable decision making at the point of impact (contextual guidance)
   Scale in proportion to the task
   Extend and magnify human expertise and cognition
   Identify resonating, human-like attributes and traits from natural language
   Deduce various language-specific or agnostic attributes from natural language
   High degree of relevant, recollection from data points (images, text, voice) (memorization and recall)
   Predict and sense with situational awareness that mimic human cognition based on experiences
   Answer questions based on natural language and specific evidence In one aspect, cognitive systems provide mechanisms for answering requests posed to these cognitive systems. The cognitive system pipeline or cognitive system is an artificial intelligence application executing on data processing hardware that answers questions pertaining to a given subject-matter domain presented in natural language. The pipeline receives inputs from various sources including input over a network, a corpus of electronic documents or other data, social media or communications platforms, data from a content creator, information from one or more content users, and other such inputs from other possible sources of input. Data storage devices store the corpus of data. A content creator creates content in a document for use as part of a corpus of data with the pipeline. The document may include any file, text, article, or source of data for use in the cognitive system. For example, a pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to the cognitive system, which implements the pipeline. The pipeline then answers the input questions using the content in the corpus of data by evaluating documents, sections of documents, portions of data in the corpus, or the like. When a process evaluates a given section of a document for semantic content, the process can use a variety of conventions to query such document from the pipeline, e.g., sending the query to the pipeline as a well-formed question which is then interpreted by the pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the pipeline receives a request, parses the request to extract the major features of the request, uses the extracted features to formulate queries, and then applies those queries to the corpus of data. Based on the application of the queries to the corpus of data, the pipeline generates a set of hypotheses by looking across the corpus of data for portions of the corpus of data that have some potential for containing a valuable response to the input question. The pipeline then performs deep analysis on the language of the request and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the pipeline. The statistical model is used to summarize a level of confidence that the pipeline has regarding the evidence that the potential response, i.e. candidate response, is inferred by the request. This process is repeated for each of the candidate responses until the pipeline identifies candidate responses that surface as being significantly stronger than others and, thus, generates a final response, or ranked set of responses, for the input request.

As mentioned above, cognitive pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional cognitive systems are capable of generating responses based on the corpus of data and the input request, verifying responses to a collection of requests for the corpus of data, correcting errors in digital text using a corpus of data, and selecting responses to requests from a pool of potential responses, i.e. candidate responses.

FIG. 1 depicts a schematic diagram of one illustrative embodiment of a cognitive system 100 implementing a request processing pipeline 108, in a computer network 102. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables request processing and response generation functionality for one or more cognitive system users via their respective computing devices 110-112. Other embodiments of the cognitive system 100 may be used with components, systems, sub-systems, and/or devices other than those that are depicted herein.

The cognitive system 100 is configured to implement a request processing pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and cognitive system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input requests to the cognitive system 100 that are answered by the content in the corpus of data 106. In one embodiment, the requests are formed using natural language. The cognitive system 100 parses and interprets the question via a request processing pipeline 108, and provides a response to the cognitive system user, e.g., cognitive system user 110, containing one or more responses to the request. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the request processing pipeline 108, which comprises a plurality of stages for processing an input question and the corpus of data 106. The request processing pipeline 108 generates answers for the input question based on the processing of the input request and the corpus of data 106.

In some illustrative embodiments, the cognitive system 100 may be the IBM Watson® cognitive system available from International Business Machines Corporation of Armonk, New York, which is augmented with the mechanisms of the illustrative embodiments described hereafter. More information about the request processing pipeline of the IBM Watson® cognitive system may be obtained, for example, from the IBM Corporation website, IBM Redbooks, and the like. For example, information about the request processing pipeline of the IBM Watson® cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as the IBM Watson® cognitive system, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system that analyzes a patient's EMR in relation to medical guidelines and other medical documentation in a corpus of information to generate a recommendation as to how to treat a medical malady or medical condition of the patient.

In particular, the cognitive system 100 implements an engagement item prediction component 120 for predicting and confirming items for a patient-doctor encounter. Engagement prediction component 120 detects a pending scheduled medical appointment for a patient, scans the patient's communication patterns and details, prompts the patient with a series of questions based on the communication patterns and details, analyzes the responses to the questions, and prepares the doctor with seed topics for the appointments based on analysis of the patient responses.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements an NL processing system 100 and NL system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller huh (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SR/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide seed topics for a medical appointment. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. Interactions between the patient 302 or user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, engagement item prediction 341 examines communications 345 or communicates with healthcare cognitive system 300 to detect a pending scheduled medical appointment between patient 302 and a doctor. The appointment may be stored in medical corpus and other source data 326 as part of data used by the doctor's practice or in patient electronic medical records (EMRs) 322 as a note about a suggested next visit or follow-up visit. Alternatively, communications data 345 may include the patient's calendar, which may be, for example, part of a cloud-based service, social media service, or the like. For instance, the patient may mention the appointment in a post on social media or may receive an email from the health care provider with a reminder of the appointment. Engagement item prediction component 341 may also implement a skill for an intelligent agents, such as Microsoft® Cortana™, Amazon® Alexa™, or Google Assistant™ intelligent agents. Thus, prediction component 320 may implement a skill that can tie into the patient's email, calendar, social media, etc. and may detect an appointment using that skill.

Engagement item prediction component 341 may integrate with instant messaging systems, real-time instant messaging systems, social networks, short messaging service (SMS) applications or services, calendaring systems, etc. Alternatively, engagement item prediction component 341 may integrate with the provider's scheduling system.

Engagement item prediction component 341 scans the communications 345 of patient 302 to identify communication patterns and details. In one embodiment, engagement item prediction component 341 identifies the patient's social identifiers, such as handles on social media networks, microblogging networks, imaging sharing networks, etc. or email addresses. In one embodiment, engagement item prediction component 341 may identify frequencies of communication at various times of day. Engagement item prediction component 341 may derive sleep patterns and activity patterns based on when the patient is active on social networks or other communications networks. For instance, engagement item prediction component 341 may determine that the patent sends messages all day and night, indicating the patient may not be sleeping.

In another embodiment, engagement item prediction component 341 may identify locations from the communications 345. For example, engagement item prediction component 341 may determine that the patient often checks into the gym. Alternatively, the patent may frequently check into fast food restaurants.

In another embodiment, engagement item prediction component 341 may examine the content of messages in communications 345 to identify health/status details. For example, engagement item prediction component 341 may detect when the patient discusses medical conditions or symptoms, such as having a headache, shakes, tiredness, dizziness, or the like. In one embodiment, engagement item prediction component 341 detects automatic postings from apps or the Internet of things (IOT), such as pedometers, smart watches, or the like, on behalf of the patient 302.

Engagement item prediction component 341 may process each of the patient's messages using natural language processing (NLP). Engagement item prediction component 341 may analyze the messages for topics, sentiment, category, etc., and extract key elements, e,g., [Health Sugar][Sugar Jiggery]. Engagement item prediction component 341 may ignore private or direct messages or specific hashtags. Alternatively, engagement item prediction component 341 may work only on public messages or message that are categorized as health (e.g., tagged). Engagement item prediction component 341 may ignore duplicate, repeated, reshared, or liked messages.

Engagement item prediction component 341 then consults healthcare cognitive system 300 with the patterns and health/status details from communications 345 to generate a series of questions to ask the patient 302. Engagement item prediction component 341 may send a request to healthcare cognitive system 300 that requests a series of questions related to the communication patterns and health/status details. Healthcare cognitive system 300 performs cognitive processing based on the communication patterns and health/status details with respect to patient electronic medical records (EMRs) 322, treatment guidance data 324, and medical corpus and other source data 326. Any information about the patient 302 that may be relevant to a cognitive evaluation of the patient by the healthcare cognitive system 300 may be included in the request.

The healthcare cognitive system 300 provides a cognitive system that is specifically configured to perform an implementation specific healthcare oriented cognitive operation. In the depicted example, this healthcare oriented cognitive operation is directed to identifying questions related to the communication patterns and health/status details of patient 302 for the purpose of identifying seed topics for the patient/doctor encounter or appointment. The healthcare cognitive system 300 operates on the request utilizing information gathered from the medical corpus and other source data 326, treatment guidance data 324, and the patient EMRs 322 associated with the patient 302 to generate one or more questions.

Healthcare cognitive system 300 may generate questions using a template or selecting similar questions from a pool of questions.

Template: How do you feel after <TOPIC>?

Pool/Set: Topic-Sugar/Dessert: How do you feel after a sugary dessert?

For example, consider Bob, a patient who is suffering from a number of ailments—a bruised leg, pre-diabetic, and sleepless nights. Eve is the primary care provider for Bob. Bob's bruised leg is not improving, and Bob schedules an appointment with Eve's office at 11:00 AM on Monday. Engagement item prediction component 341 detects the pending appointment, retrieves Bob's social identifiers, and scans Bob's communication patterns and details in communications 345.

Figure 4:
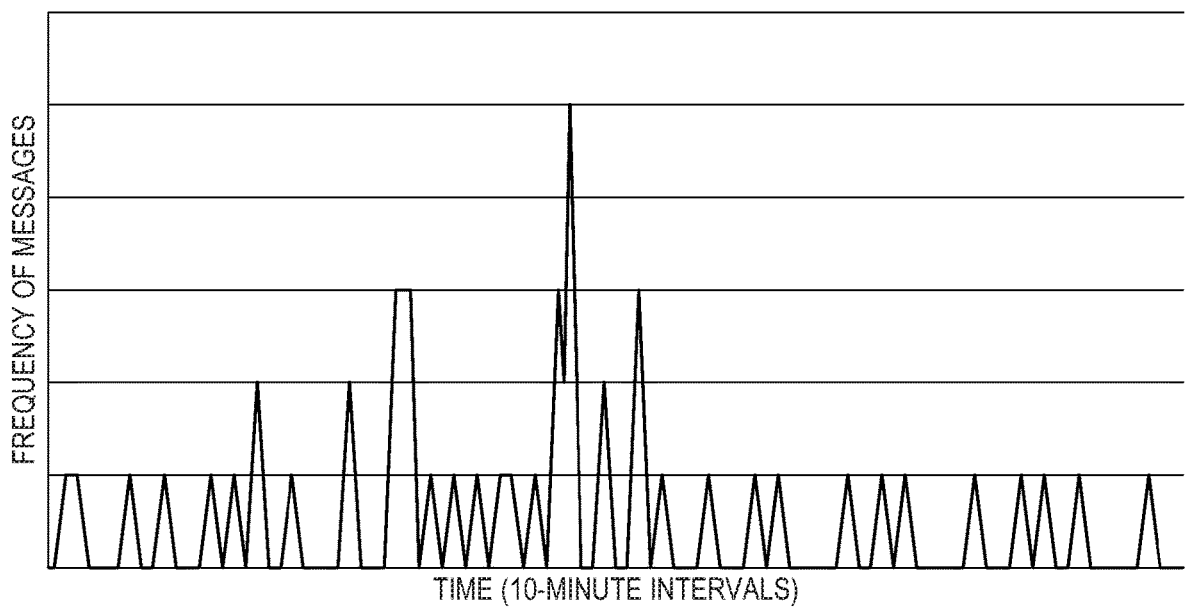
FIG. 4 depicts an example of communication patterns in accordance with an illustrative embodiment.

FIG. 4 depicts an example of communication patterns in accordance with an illustrative embodiment. Engagement item prediction component 341 recognizes that Bob sends messages all day and night.

Figure 5:
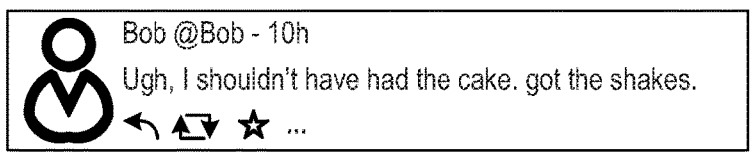
FIG. 5 depicts an example of a specific communication in accordance with an illustrative embodiment.

FIG. 5 depicts an example of a specific communication in accordance with an illustrative embodiment. Engagement item prediction component 341 identifies the message is related to health or status.

Engagement item prediction component 341 sends the communication pattern, indicating that the patient sends messages all day and night (ten messages an hour after hours), and the health/status details, indicating that the patient got the shakes as a result of eating cake, to healthcare cognitive system 300. Based on this information, healthcare cognitive system 300 generates questions related to the frequency of messages as follows: "Do you use electronics late at night?" and "How is your sleep quality?" Healthcare cognitive system 300 generates a question related to the health status details as follows: "Do you feel jittery after eating dessert?" Engagement item prediction component 341 then sends the generated questions 311 to patient 302 and receives responses 312 from patient 302.

In one embodiment, engagement item prediction component 341 sends the questions 311 to a computing device of patient 302 and receives responses 312 using a common communication medium, such as short messaging service (SMS) message, electronic mail, chat service, or telephone interactive voice response (IVR) system. In another embodiment, engagement item prediction component 341 sends the questions 311 to patient 302 and receives responses 312 using a social media network. For instance, if engagement item prediction component 341 determines that patient 302 uses a particular social network with high frequency at a specific time of day, then engagement item prediction component 341 may communicate with the patient 302 using that social network at the specific time of day. In yet another embodiment, engagement item prediction component 341 may communicate send questions 311 and receive responses 312 through a smartphone app or through an intelligent assistant executing on a smartphone device.

Figure 6:
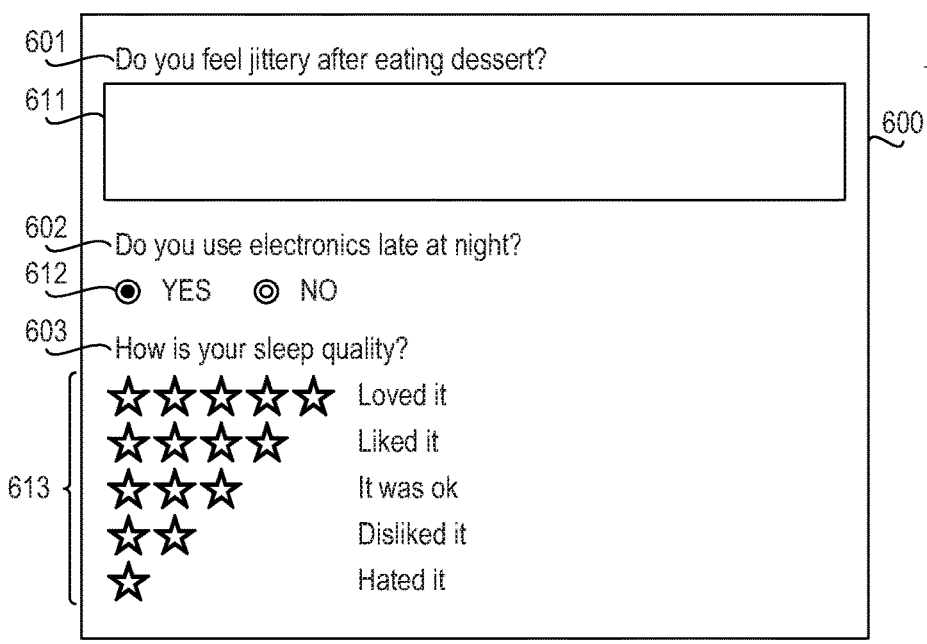
FIG. 6 depicts an example of a user interface for presenting questions and receiving patent responses in accordance with an illustrative embodiment.

FIG. 6 depicts an example of a user interface for presenting questions and receiving patent responses in accordance with an illustrative embodiment. User interface 600 may be presented in a computing device of the patient, such as a computer or smartphone device or through a Web site. User interface 600 includes questions 601, 602, 603 and user interface components 611, 612, 613 that allow the patient to provide responses through user interface 600. For example, user interface component 611 allows the patient to write a response in natural language, user interface component 612 is a radio button for selecting one of a finite number of choices, and user interface component 613 provides a star rating system. Other user interface components may also be used, such as check boxes, drop-down lists, slide bars (e.g., pain scale), dials, body reference, etc.

In the above example, the patient may write a response into user interface component 611 as follows: "Yes, whenever I eat chocolate cake with extra frosting." The user may also select the "YES" radio button in user interface component 612 and select the "Loved it" or 5-start selection in user interface component 613.

Engagement item prediction component 341 may provide a trajectory of prompts/responses through multiple surveys. In another embodiment, engagement item prediction component 341 may prompt the patient with questions on a repeated schedule.

Engagement item prediction component 341 receives the patient's responses 312 and sends a request to healthcare cognitive system 300 to generate a set of seed topics for the pending appointment. For example, based on the patient responses, healthcare cognitive system 300 generates seed topics 313 for user 306. The user 306 may be the doctor or other staff at the primary care provider or other healthcare provider. The doctor may then use the seed topics to direct the patient/doctor interaction during the limited time of the appointment. For example, for the above example, given Bob's responses, the seed topics 313 may include the following: Sugar/Diabetic issues and Sleep issues—Electronics usage. User 306 may also see the questions 311 and responses 312 to assist in guiding the patient/doctor interaction. In one embodiment, user 306 may also see the time taken to complete the responses and/or the time the survey was taken.

The present invention may be a system, a method, and/or a computer program product. The computer program product may include a computer readable storage medium (or media) having computer readable program instructions thereon for causing a processor to early out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

FIG. 7 is a flowchart illustrating operation of a mechanism for predicting engagement items for care providers in accordance with an illustrative embodiment. Operation begins (block 700), and the mechanism detects a scheduled appointment between a patient and a doctor (block 701). The mechanism scans patient communication patterns and details for indicators of a medical condition (block 702). The mechanism generates a set of one or more questions related to the medical condition (block 703) and presents the questions to the patient (block 704). The mechanism then receives responses to the questions from the patient (block 705) and generates seed topics for the doctor based on the patient responses (block 706). The mechanism then presents the seed topics to the doctor prior to the appointment (block 707). Thereafter, operation ends (block 708).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide a mechanism for verification of clinical hypothetical statements based on dynamic cluster analysis. The mechanism of the illustrative embodiments generates a parse tree for each sentence in a patient's electronic medical record. The mechanism identifies a hypothetical phrase or statement from the parse tree and identifies a hypothetical condition corresponding to the phrase. The mechanism then identifies attributes associated with the hypothetical condition. The mechanism of the illustrative embodiments uses cohort or cluster analysis to identify patients that are similar and matches noun phrases and attributes from the cluster to those of the current patient. Based on the number of matching noun phrases and attributes between the current patient and the patients in the cluster, the mechanism determines whether the hypothetical condition is confirmed to be true.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions which are executed by the at least one processing unit and configure the at least one processing unit to implement an engagement item prediction component and a healthcare cognitive system which operate for predicting engagement items for a care provider, the method comprising:

detecting, by an engagement item prediction component integrated within an intelligent assistant executing on a user device associated with a patient, a scheduled appointment between the patient and a doctor based on communication data from an electronic mail system, a messaging application, and a social media system, wherein the intelligent assistant accesses the communications data;

scanning, by the engagement item prediction component, the communication data to identify a communication pattern and details of patient communications for indicators of a medical condition of the patient;

generating, by the healthcare cognitive system, a set of one or more questions related to the medical condition;

presenting, by the engagement item prediction component, the set of one or more questions to the patient via the intelligent assistant;

receiving, by the engagement item prediction component, one or more responses to the set of one or more questions from the patient via the intelligent assistant;

generating, by the healthcare cognitive system, one or more seed topics based on the one or more responses; and presenting, by the healthcare cognitive system, the one or more seed topics to the care provider for the scheduled appointment.

2. The method of claim 1, wherein the communication pattern comprises a frequency of patient messages, time-of-day of patient messages, and location information associated with patient messages.

3. The method of claim 2, wherein scanning the communications data comprises determining sleep patterns and electronic device usage based on the communication pattern.

4. The method of claim 2, wherein scanning the communication data comprises determining eating and exercise habits based on the communication pattern.

5. The method of claim 1, wherein scanning the communication data comprises performing natural language processing on patient messages within the electronic mail system, the messaging application, and the social media system.

6. The method of claim 5, wherein performing natural language processing on the patient messages comprises identifying topics, sentiment, category, and key elements of the patient messages.

7. The method of claim 1, wherein generating the set of one or more questions related to the medical condition comprises generating the one or more questions using templates.

8. The method of claim 7, wherein generating the set of one or more questions related to the medical condition comprises selecting the one or more questions from a pool of questions associated with health topics.

9. The method of claim 1, wherein presenting the set of one or more questions to the patient comprises presenting a trajectory of questions and responses in multiple surveys.

10. The method of claim 1, wherein generating the one or more seed topics comprises:
sending a request to a healthcare cognitive system comprising the one or more responses; and
analyzing, by the healthcare cognitive system, the one or more responses to identify the one or more seed topics.

11. The method of claim 1, wherein the communication data comprises automatic postings from apps or the Internet of Things on behalf of the patient.

12. The method of claim 1, wherein the intelligent assistant accesses public messages within the communication data and ignores private messages within the communication data.

13. A computer program product comprising a computer readable storage medium having a computer readable program stored therein, wherein the computer readable program comprises instructions, which when executed on at least one processor of a computing device causes the computing device to implement an engagement item prediction component and a healthcare cognitive system which operate for predicting engagement items for a care provider, wherein the computer readable program causes the computing device to:
detect, by an engagement item prediction component integrated within an intelligent assistant executing on a user device associated with a patient, a scheduled appointment between Dr' the patient and a doctor based on communications data from an electronic mail system, a messaging application, and a social media system, wherein the intelligent assistant accesses the communications data;
scan, by the engagement item prediction component, the communications data to identify a communication pattern and details of patient communications for indicators of a medical condition of the patient;
generate, by the healthcare cognitive system, a set of one or more questions related to the medical condition;
present, by engagement item prediction component, the set of one or more questions to the patient via the intelligent assistant;
receive, by the engagement item prediction component, one or more responses to the set of one or more questions from the patient via the intelligent assistant;
generate, by the healthcare cognitive system, one or more seed topics based on the one or more responses; and
present, by the healthcare cognitive system, the one or more seed topics to the care provider for the scheduled appointment.

14. The computer program product of claim 13, wherein the communication pattern comprises a frequency of patient messages, time-of-day of patient messages, and location information associated with patient messages.

15. The computer program product of claim 13, wherein scanning the communication data comprises performing natural language processing on patient messages within the electronic mail system, the messaging application, and the social media system.

16. The computer program product of claim 15, wherein performing natural language processing on the patient messages comprises identifying topics, sentiment, category, and key elements of the patient messages.

17. The computer program product of claim 13, wherein generating the set of one or more questions related to the medical condition comprises generating the one or more questions using templates.

18. The computer program product of claim 17, wherein generating the set of one or more questions related to the medical condition comprises selecting the one or more questions from a pool of questions associated with health topics.

19. The computer program product of claim 13, wherein generating e one or more seed topics comprises:
sending a request to a healthcare cognitive system comprising the one or more responses; and
analyzing, by the healthcare cognitive system, the one or more responses to identify the one or more seed topics.

20. A computing device comprising:
at least one processing unit; and
a memory coupled to the at least one processing unit, wherein the memory comprises instructions, which when executed on the at least one processor causes the computing device to implement an engagement item prediction component and a healthcare cognitive system which operate for predicting engagement items for a care provider, wherein the instructions cause the computing device to:
detect, by an engagement item prediction component intelligent assistant executing on a user device associated with a patient, a scheduled appointment between the patient and a doctor based on communications data from an electronic mail system, a messaging application, and a social media system, wherein the intelligent assistant accesses the communications data;
scan, by the engagement item prediction component, the communications data to identify a communication pattern and details of patient communications for indicators of a medical condition of the patient;
generate, by the healthcare cognitive system, a set of one or more questions related to the medical condition;
present, by engagement item prediction component, the set of one or more questions to the patient via the intelligent assistant;
receive, by the engagement item prediction component, one or more responses to the set of one or more questions from the patient via the intelligent assistant;
generate, by the healthcare cognitive system, one or more seed topics based on the one or more responses; and
present, by the healthcare cognitive system, the one or more seed topics to the care provider for the scheduled appointment.

\* \* \* \* \*